US005910455A

United States Patent [19]
Maddern et al.

[11] Patent Number: 5,910,455
[45] Date of Patent: Jun. 8, 1999

[54] HAND CLEANSER

[75] Inventors: Peter Maddern, N. Wales, United Kingdom; Serge Khalifa, Worben, Switzerland

[73] Assignee: Kimberly Clark Corp., Neenah, Wis.

[21] Appl. No.: 08/712,737

[22] Filed: Sep. 12, 1996

[51] Int. Cl.$^6$ .................................................. B32B 5/02
[52] U.S. Cl. ........................ 442/60; 424/402; 424/404; 442/59; 442/123; 442/340
[58] Field of Search ................................. 424/402, 404; 442/59, 60, 123, 340

[56] References Cited

U.S. PATENT DOCUMENTS

| | | | |
|---|---|---|---|
| Re. 29,649 | 5/1978 | Farnsworth | 252/171 |
| 3,819,405 | 6/1974 | Engle | 117/138.8 |
| 4,436,780 | 3/1984 | Hotchkiss et al. | 428/198 |
| 4,511,488 | 4/1985 | Matta | 252/162 |
| 4,533,487 | 8/1985 | Jones | 252/170 |
| 4,640,719 | 2/1987 | Hayes et al. | 134/40 |
| 4,659,609 | 4/1987 | Lamers et al. | 428/194 |
| 4,758,377 | 7/1988 | Iiding | 252/556 |
| 4,778,048 | 10/1988 | Kaspar et al. | 206/205 |
| 4,833,003 | 5/1989 | Win et al. | 428/198 |
| 5,300,154 | 4/1994 | Ferber et al. | 134/26 |
| 5,320,772 | 6/1994 | Tricca | 252/160 |
| 5,344,007 | 9/1994 | Nakamura et al. | 206/205 |
| 5,415,813 | 5/1995 | Misselyn et al. | 252/547 |
| 5,416,253 | 5/1995 | Weltman et al. | 588/259 |
| 5,614,484 | 3/1997 | Panandiker | 510/102 |
| 5,683,971 | 11/1997 | Rose et al. | 510/130 |

FOREIGN PATENT DOCUMENTS

| | | |
|---|---|---|
| 354 027 | 2/1990 | European Pat. Off. . |
| 0 615 720 | 9/1994 | European Pat. Off. . |
| 641 346 | 2/1984 | Switzerland . |
| 1603147 | 11/1981 | United Kingdom . |
| 93/02169 | 2/1993 | WIPO . |

OTHER PUBLICATIONS

Bush Boake Allen Solvent Informtion, Technical Bulletin, TB04.92, Issue 01, Jul. 1992.

Citrosperse™ Microemulsifiers Publication, 52–0035–301 Mar. 1993, ICI Surfactants, Wilmington, Delaware.

Ellis & Everard Cargo Fleet Site Publication, Sheet No. F20, Issue 1, Aug. 1992, Ellis & Everard (UK) Ltd.

Chemax, Inc. Product Data, Greenville, SC, MSDS Chemax DLS–5878, Nov. 1990, Product Data DLC–001, DLC–002—Jul. 1987, DLC–004, Jun. 1987.

Tomah Products Data Sheet, Exxon Chemical, JM11/0005.

Caresonic, CARESOL 8908, Health and Safety Data Sheet, Issue 2, Oct. 1989.

Suggested Formulas Incorporating d–LIMONENE, Specialty Chemical Division, Harcros Chemicals Inc. Kansas City, KS, May 1989.

Westvaco Diacid 1550 Dicarboxylic Acid Publication, Westvaco Chemical Division, Charleston Heights, SC.

DeSoto, Inc., Chemical Specialties Division, Fort Worth, TX, Data Sheets, I–3076 and I–3075, Mar. 1988.

Stephan Technical Information, "Limonene in Cleaners", Stepan Company, Northfield, IL, Apr. 1987.

Derwent Publications Ltd., London, GB; AN 95–078287; XP002023864 & JP,A,07 003 297 (Nikka Kagaku KK), Jan. 6, 1995.

Derwent Publications Ltd., London, GB; AN 94–148165; XP002023865 & JP,A,06 093 296 (Olympus Optical Co.), Apr. 5, 1994.

*Primary Examiner*—James J. Bell
*Attorney, Agent, or Firm*—Karl V. Sidor

[57] ABSTRACT

The present invention provides an aqueous cleanser formulation comprising a blend of paramenthadienes together with one or more surfactants and/or solubilisers. Such a formulation has been found to be capable of removing a wide range of heavy soils from the skin surface whilst leaving minimal residual odour.

9 Claims, No Drawings

HAND CLEANSER

The present invention relates to a cleanser, in particular a so-called "waterless" hand cleanser, and an abrasive hand cleansing article impregnated with such a cleanser.

Conventional hand cleansing formulations contain solvents and/or surfactants capable of solubilising or emulsifying soils present on the skin surface. The cleansing power of such formulations is however limited, particularly when dealing with the removal of various heavy, ingrained soils such as may be encountered by those working in industry.

A number of hand cleansers currently being used are in the form of a gel which may contain both polar and non-polar ingredients blended together to achieve removal of a variety of soils from the skin surface. These often contain abrasive particles which scour the skin surface to aid in the removal of embedded soils. One disadvantage associated with the use of such gels is the need to wash-off the gel residue or excess cleanser from the skin following use. This means that the operation of hand cleansing takes longer and, in the case of industrial hand cleansing, this ultimately increases costs.

A further disadvantage associated with the use of gels is that, depending on the formulation, these have a tendency to remove the skin's natural protective lipids, particularly when the cleanser is used repeatedly, leaving the skin with no protection against dehydration once the gel residue has been rinsed off. This is a particular problem in areas of low humidity.

One solution to this problem has been presented in the form of "waterless" formulations which can be used to cleanse the skin surface without the need to use any added water during the actual hand cleansing process. A "waterless" formulation of this type is described in EP-A-615720 in which a d-limonene based formulation is used for cleansing the skin. However, such a formulation has a particularly high citrus fragrance, leaving the hands with an undesirable and long-lasting residual orange citrus odour following use. Furthermore, such a formulation is thought to have only a limited tendency to re-fat or moisturise the skin after cleansing. D-limonene is extracted from orange peel and is hence relatively costly. Moreover, its availability is dependent upon crop yields and is thus subject to fluctuation.

There thus exists a need for an improved "waterless" cleanser with low residual odour which is capable of removing a wide range of heavy soils from the skin surface, whilst preferably at the same time effectively moisturising the skin.

It has now surprisingly been found that a blend of paramenthadienes is capable of acting as an effective solvent for oily, greasy deposits whilst at the same time serving to moisturise the skin and without leaving any long-lasting residual odour on the skin surface.

According to one aspect, the present invention thus provides an aqueous cleanser formulation comprising a blend of paramenthadienes, preferably in an amount of from 1 to 20% by weight, together with one or more surfactants and/or solubilisers.

Suitable for use in the formulation of the invention is a blend of paramenthadienes comprising α-terpinene, γ-terpinene, iso-terpinolene and camphene, which may be present in amounts of from 30 to 50%, from 10 to 256, from 15 to 35% and from 1 to 10% by weight respectively. Preferably, the α-terpinene is present in an amount of from 35 to 45% by weight, the γ-terpinene in an amount of from 15 to 20% by weight, the iso-terpinolene in an amount of from 20 to 25% by weight and the camphene in an amount of from 3 to 8% by weight.

The paramenthadiene blend may further comprise one or more of the following paramenthadienes: limonene, terpinolene, α-phellandrene and β-phellandrene, which may each be present in an amount of up to 10% by weight, preferably up to 5% by weight.

Particularly suitable for use in the formulation of the invention is a blend of paramenthadiene isomers available from Bush Boake Allen Ltd. under the trade name TABS DS. This is a mixture of naturally occurring paramenthadienes comprising α-terpinene, γ-terpinene, iso-terpinolene, limonene, terpinolene, α-phellandrene, βphellandrene and camphene.

Preferred formulations in accordance with the invention include those in which the paramenthadiene blend is present in an amount of from 1 to 10 wt. %, particularly from 5 to 10 wt. %.

The paramenthadiene blend acts as an effective solvent for a wide range of heavy soils, including oily, greasy deposits such as petroleum oils, vegetable oils, grease and tar, and may be used in combination with any suitable solubiliser and/or surfactant or surfactant blend. Solubilisers suitable for use in the formulation of the invention include oily emulsifiers eg. PEG-40 Hydrogenated Castor Oil and PPG-1-PEG-9 Lauryl Glycol Ether, which serve to lay down a protective oily but dry film on the skin thereby minimising subsequent dehydration of the skin.

Surfactants suitable for use in the formulation of the invention may be non-ionic, ionic or amphoteric in nature, the only requirement being that it serves to emulsify with the paramenthadienes and any other components present in the formulation which require to be emulsified. Any conventional surfactants or surfactant blends may be used.

The solubilisers may be present in an amount of up to 15 wt %. An amount of around 12 wt. a has been found to be preferable.

In a preferred embodiment, the formulations in accordance with the invention further comprise one or more additional organic solvents in an amount of from 1 to 10 wt. %, preferably from 2 to 6 wt. W. Such solvents are preferably capable of solubilising polar contaminants such as paint and adhesives from the skin, thereby improving the cleansing efficiency of the formulation. Suitable co-solvents include ethers such as PPG-2 Methyl Ether, PPG-1 n-Propyl Ether, PPG-2 n-Butyl Ether and PPG-2 Dimethyl Ether, and lactates such as Ethyl Lactate, Butyl Lactate and Ethylhexyl Lactate.

Additional components which may be present in the formulations of the invention include anti-oxidants such as butylated hydroxy toluene (BHT); fragrances, such as orange citrus fragrance, lemon fragrance or floral fragrance; emollients, such as Aloe Barbadensis Gel; anti-microbial agents, such as Methyldibromo Glutaronitrile, conveniently carried on a carrier such as Phenoxyethanol; or other standard anti-oxidants, emollients and preservatives.

Anti-oxidants such as BHT have been found to stabilise the paramenthadiene mixture against oxidation and may be present in the formulation in an amount of up to 0.5% by weight.

The formulations in accordance with the invention may be prepared in any conventional manner, eg. by simple admixture of the components. Conveniently, as a first step the paramenthadiene blend may be mixed with the surfactants and/or solubilisers and water, with any additional components subsequently being added with additional mixing. Paramenthadienes are readily available as a by-product of the pulping of pine trees and are therefore a renewable resource.

Abrasive hand cleansing materials, more commonly known as wet-wipes, are capable of cleansing embedded soils from the skin without the need for rinsing. Such materials are predominantly made from airlaid cellulosic fibres which may be saturated with a suitable cleansing solution. The formulations defined above have been found to be particularly effective in removing heavy soils from the hands when incorporated into such abrasive hand cleansing materials.

According to a further aspect, the invention thus provides an abrasive cleansing material comprising a substrate having at least one abrasive surface, the substrate being impregnated with an aqueous cleansing fluid comprising a blend of paramenthadienes together with one or more surfactants and/or solubilisers. Cleansing action is achieved by the cleansing fluid and abrasive action is achieved by the abrasive surface of the substrate, enabling the material to produce a mild scrubbing action on the skin and thus aid in removal of ingrained soils.

The substrate may comprise a cloth-like towel consisting of a system of pores able to absorb and retain the aqueous cleansing fluid, yet capable of readily releasing the fluid onto the skin surface during use.

Conveniently, a plurality of abrasive towels containing the cleansing formulation are provided, either in a stack or in a continuous perforated roll, the individual towels being readily separable along each line of perforation. The towels may be provided in a container to which the aqueous formulation is then added to moisten the towels. Capillary action ensures that the cleansing fluid is evenly distributed throughout the stack or roll of towels, each towel containing an amount of cleanser sufficient to thoroughly cleanse the skin. Alternatively, the abrasive material is pre-soaked prior to or during the operation of converting it into stacks or rolls.

Non-woven thermoplastic webs may be used as an abrasive substrate for the cleansing formulation. These can be made either by meltblowing or spunbonding, techniques which are both well-known in the art, see for example U.S. Pat. No. 3978185 and U.S. Pat. No. 3692618.

The technique of meltblowing is preferred for producing the abrasive cleansing materials of the invention. This involves extruding a multiplicity of continuous thermoplastic polymer strands through a multiplicity of die orifices in a downward direction, the extruded polymer strands being broken up and dispersed into individual fibres by a forced airstream before being deposited onto a moving collecting surface. In addition, the fibres are substantially cooled by the air to prevent any significant bonding between individual fibres. Bonding of the web to retain integrity and strength occurs as a separate downstream operation. Meltblown webs formed in this way are characterised by their softness, bulk, absorbency and low porosity with a degree of abrasion resistance.

Meltblown webs or sheets suitable for the wipes of the present invention are well-known in the non-wovens industry. Typically, such materials are made of polypropylene, although other thermoplastic polymers, such as polyethylene, poly(ethylene terephthalate), poly(butylene terephthalate), polymethylpentene, polycaprolactam and propylene ethylene co-polymer can also be used. Preferably, the polymers are present in an amount of from 15 to about 200 grams per square meter (gsm) of the material, more preferably about 35 gsm. The unique properties of meltblown webs enable retention of the liquid cleanser as well as ready transfer of the liquid to adjacent contacting meltblown webs through capillary action. At the same time, the web is able to readily transfer the liquid cleanser onto the skin during use and also serves to trap removed soils between the fibres following cleansing as well as to wick liquids away from the skin.

One or more meltblown layers may, if desired, be supported on a supporting web, which is preferably spunbonded, in order to increase the strength of the resulting material. Such a material exhibits the strength of a spunbonded web whilst maintaining the abrasiveness of the meltblown layer.

Preferred abrasive substrates are dual texture macrofibre/microfibre meltblowns such as described in U.S. Pat. No. 4775582, U.S. Pat. No. 4833003, U.S. Pat. No. 4853281 and EP-A-256950. The terms "macrofibre" and "microfibre" are used herein to distinguish between webs having different pore size distributions. "Macrofibre" meltblown refers to webs having less than 65% of the pore volume attributable to pores having a size of from about 20 to about 60 microns. "Microfibre" meltblown refers to webs in which at least 65% of the pore volume is attributed to pores having a size of from about 20 to about 60 microns.

Dual texture macrofibre/microfibre polypropylene meltblowns comprising 28% by weight macrofibres and 72% by weight microfibres are particularly preferred.

The amount of liquid cleanser within each wipe or sheet may be from 100 to about 500% by weight, suitably from about 150 to about 500% by weight, preferably from about 200 to about 450% by weight, more preferably from about 340 to about 400% by weight, and yet more preferably about 350% by weight. If the amount of cleanser is too low then the wipe will be too dry and will not adequately cleanse the skin. If the amount of cleanser is too high then the wipe will be too soggy and may tend to simply "push" the soily deposits over the skin. The cleanser fluid may also begin to pool in the container.

The invention will now be further described by way of the following non-limiting Examples:

EXAMPLE 1

Hand Cleanser Formulation

|  | % by weight |
| --- | --- |
| Blend of paramenthadienes (TABS DS terpene mixture) | 7.00 |
| PPG-2 Methyl Ether | 4.00 |
| PPG-1-PEG-9 Lauryl Glycol Ether | 6.00 |
| PEG-40 Hydrogenated Castor Oil | 6.00 |
| Phenoxyethanol | 0.16 |
| Methyldibromo Glutaronitrile | 0.04 |
| Aloe Barbadensis Gel | 0.01 |
| Parfum (Orange citrus fragrance) | 1.40 |
| Aqua (water) | 75.39 |

The above ingredients were mixed in the given proportions to produce a liquid cleanser. Use of the cleanser was found to be particularly effective in removing asphalt-based artificial soiling agent, SCRUB CRUD®, TUFLUBE®, marker pen ink and non-dried acrylic-based paint in subjective hand wiping tests. Any excess cleanser did not require water for removal from the hands but was simply wiped off with a towel or cloth.

The cleanser left hands clean, soft and having an initial pleasant citrus scent which dissipated rapidly leaving a minimal pleasant "soapy" residual odour.

EXAMPLE 2

Hand Cleanser Formulation

| | % by weight |
|---|---|
| Blend of paramenthadienes (TABS DS terpene mixture) | 7.00 |
| PEG-40 Hydrogenated Castor Oil | 6.00 |
| PPG-1-PEG-9 Lauryl Glycol Ether | 6.00 |
| PPG-2 Methyl Ether | 4.00 |
| Parfum (Orange citrus fragrance) | 1.20 |
| BHT | 0.462* |
| Phenoxyethanol | 0.16 |
| Methyldibromo Glutaronitrile | 0.04 |
| Aloe Barbadensis Gel | 0.01 |
| Aqua (water) | 75.128 |

*in addition to the estimated 0.038% by weight of BHT already present in the formulation from BHT present in the blend of paramenthadienes and the fragrance to give a total BHT level of 0.5% by weight.

The above ingredients were mixed in the given proportions to produce a liquid cleanser.

The cleanser left hands clean, soft and having an initial pleasant citrus scent which dissipated rapidly leaving a minimal pleasant "soapy" residual odour.

EXAMPLE 3

"Wet Wipes" Containing Cleanser Formulation

Dual texture macrofibre/microfibre polypropylene meltblowns (1.02 osy) comprising 28 wt. % macrofibres and 72 wt. % microfibres were produced in accordance with EP-A-0573277. These were then impregnated with the cleanser formulations of Examples 1 and 2, in each case in a ratio of 3.5 g of the formulation per g of the meltblown.

When used in hand wiping tests, there was no need to use any cloth for removal of excess cleanser. Use of the "wet wipes" left hands clean, soft and having an initial pleasant citrus scent which dissipated rapidly leaving a minimal pleasant "soapy" residual odour.

EXAMPLE 4

Cleaning Efficacy and Skin Moisturisation of "Wet Wipe" Containing Cleanser Formulation The dual texture meltblown of Example 3 impregnated in a 3.5:1 ratio with the cleanser formulation of Example 2 was tested as follows:

1. Cleaning Efficacy

The wet wipe was tested for cleaning efficacy using a Gardner washability apparatus. Various soils were applied to a square 50 mm$^2$ section of a textured vinyl substrate. The soiled panels were then mechanically cleaned with the abrasive side of the wet wipe wrapped around a block weighing 469 g, this weight being designed to simulate the effect of pressure applied when cleaning the hands. The panels were cleaned for a fixed number of cycles depending on the particular soil under test.

The cleaned soiled areas of the vinyl substrate panels were measured using a colourmeter and compared to the initial reflectance (whiteness) of the vinyl substrate prior to soiling. The final reflectance after cleaning was taken to be the average of several readings. The cleaning efficiency is the ratio of final reflectance compared to initial reflectance. Typically, the test was repeated five times to obtain an average result.

Results:

| Contaminant | Cleaning Efficiency (%) |
|---|---|
| SCRUB CRUD ® (artificial soil) | 80.6 |
| Marker pen | 69.2 |
| Cellulose paint | 71.3 |
| Printers' ink | 38.4 |
| TEROSON car underseal | 29.5 |
| Silicone sealant | 30.8 |
| Car wax | 83.6 |
| Hydraulic oil | 100 |
| Automotive grease | 71.9 |
| Oil-based paint | 63.7 |
| Used motor oil | 91.7 |
| Emulsion paint | 89.5 |
| Gloss paint | 75.9 |
| Carbon powder | 86.7 |

2. Skin Moisturisation

A test was carried out to determine the effect of the wet wipe on the conductance of the skin compared to conventional products. Conductance is one measure of the level of moisture in the skin. The higher the reading, the higher the moisture content of the stratum corneum.

Twenty subjects were employed for the test. Baseline conductance measurements were taken of washed and dried skin at each of 4 sites (2 left and 2 right) on the subjects, arms. Five readings were taken per site. Each site was wiped with the product. After 30 minutes, conductance was measured at each site. The difference between the average test measurement and the average baseline measurement was taken.

Results:

| Hand Cleaning product | Post/pre conductance ratio (%) |
|---|---|
| Wet wipe in accordance with the invention | 114 |
| Hand cleaning gel 1 (TUFNEGA available from Deb Limited, UK) | 100 |
| Hand cleaning gel 2 (SWARFEGA available from Deb Limited, UK) | 97 |
| Water | 91 |

These results indicate that the wet wipe in accordance with the invention promotes skin moisturisation.

EXAMPLE 5

Hand Cleanser Formulation

| | % by weight |
|---|---|
| Blend of Paramenthadienes (TABS DS terpene mixture) | 7.00 |
| PPG-2 Methyl Ether | 4.00 |
| PPG-1-PEG-9 Lauryl Glycol Ether | 6.00 |
| PEG-40 Hydrogenated Castor Oil | 6.00 |
| Phenoxyethanol | 0.80 |
| Methyldibromo Glutaronitrile | 0.04 |
| Aloe Barbadensis Gel | 0.01 |
| Parfum (orange citrus fragrance) | 1.20 |
| BHT | 0.087* |
| Aqua (water) | 74.863 |

*in addition to the estimated 0.038% by weight of BHT already present in the formulation from BHT present in the blend of paramenthadienes and the fragrance to give a total BHT level of 0.125% by weight.

EXAMPLE 6

Cleaning Efficacy of "Wet Wipe" Containing Cleanser Formulation

The dual texture meltblown of Example 3 impregnated in a 3.5:1 ratio with the cleanser formulation of Example 5 was tested for cleaning efficacy as follows:

Test 1

The cleaning efficacy of the wet wipe was evaluated using the Gardner washability apparatus according to the method described in Example 4.

Results:

|             | Cleaning efficiency (%) | | | |
| --- | --- | --- | --- | --- |
| Contaminant | Batch 1 | Batch 2 | Batch 3 | Batch 4 |
| SCRUB CRUD ® | 78.3 | 68.8 | 77.7 | 78.5 |
| Automotive grease | 68.4 | 72.1 | 80.1 | 73.2 |
| Automotive paint | 67.3 | 71.9 | 63.8 | 65.1 |

Test 2

The wet wipe was evaluated by a panel of 10 people using soils chosen to represent a range of industrial contaminants normally encountered in the workplace. The procedure used was that according to U.S. Military Specification Mil-H-43606 in which a fixed amount of contaminant was applied to the hands and allowed to remain for a certain period of time. The hands were then cleaned for a certain period of time after which the cleaning ability was evaluated.

The wet wipes were rated visually by the panellists for cleaning efficiency based on the following rating. The higher the number, the better the cleaning efficiency:

| Rating scale | | |
| --- | --- | --- |
| 4 | Excellent removal | >75% |
| 3 | Good removal | 50–75% |
| 2 | Fair removal | 25–50% |
| 1 | Poor removal | <25% |

The rate was calculated from the cleaning efficiency rating after a prescribed time as follows:
% of total possible score
 time in minutes $$\text{where } \% \text{ of total score} = \frac{(\text{Efficiency rating} - 1)}{3} \times 100$$

The rate is a calculation of the amount of product removed in a fixed time. The higher the number, the faster the product cleans the hands.

Results:

| Soil | Cleaning efficiency | Rate |
| --- | --- | --- |
| Urban soil (Sander-Lambert Synthetic Urban Soil) | 2.7 | 57 |
| Ingrained dirt (asphalt) | 3.0 | 66 |
| Auto Grease | 3.6 | 87 |
| Silicone glue | 3.8 | 93 |
| Printing ink | 2.5 | 50 |
| Marking pen | 3.3 | 76 |
| Oil paint | 2.6 | 50 |

The wet wipe was also evaluated using a Gardner washability apparatus. The soils were applied to a 4"×18" textured vinyl substrate. The soiled panels were then mechanically cleaned with the wet wipe wrapped around a block. The panels were cleaned with the abrasive side of the dual textured meltblown for a fixed number of cycles depending on the soil under test. The cleaning was stopped at the midpoint and the wipe removed, repositioned to a clean area and replaced before resuming to prevent saturation or clogging of the wipe.

Soil removal was evaluated both visually according to the rating scale given above and using a reflectometer. For the latter, the initial reflectance (whiteness) of the panel was measured prior to soiling. Several readings were taken and averaged. The final reflectance was measured after cleaning by taking the average of several readings. The cleaning efficiency is the ratio of final reflectance over initial reflectance.

Results:

| Soil | % soil removal based on reflectance (average of 3) | % soil removal based on visual assessment |
| --- | --- | --- |
| Urban soil (Sander-Lambert Synthetic Urban Soil) | 84 | 90 |
|  |  | 85 |
|  |  | 90 |
| Ingrained dirt (asphalt) | 13 | 65 |
|  |  | 65 |
|  |  | 65 |
| Auto Grease | 84 | 80 |
|  |  | 85 |
|  |  | 85 |
| Silicone glue | 64 | 75 |
|  |  | 75 |
|  |  | 70 |
| Printing ink | 44 | 85 |
|  |  | 85 |
|  |  | 85 |
| Marking pen | 40 | 40 |
|  |  | 40 |
|  |  | 40 |
| Oil paint | 36 | 50 |
|  |  | 65 |
|  |  | 60 |

What is claimed is:

1. An abrasive hand cleansing material comprising a substrate having at least one abrasive surface, the substrate being impregnated with an aqueous hand cleansing formulation comprising from about 1 to 20% by weight of a blend of paramenthadienes, together with one or more oily emulsifiers and from 1 to 10% by weight of one or more organic co-solvents capable of solubilizing polar contaminants, the organic co-solvents being selected from the group consisting of PPG-2 methyl ether. PPG-1 n-propyl ether, PPG-2 n-butyl ether, PPG-2 dimethyl ether, ethyl lactate, and ethylhexyl lactate.

2. The abrasive hand cleansing material of claim 1, wherein the substrate comprises a dual texture macrofibre/microfibre meltblown.

3. The abrasive hand cleansing material of claim 2, wherein the meltblown comprises 28% by weight macrofibres and 72% by weight microfibres.

4. The abrasive hand cleansing material of claim 1 wherein the ratio by weight of hand cleansing formulation to substrate is about 3.5:1.

5. The abrasive hand cleansing material of claim 1 wherein the blend of paramenthadienes comprises α-terpinene, γ-terpinene, iso-terpinolene and camphene.

6. The abrasive hand cleansing material of claim 5, wherein the blend of paramenthadienes further comprises one or more of limonene, terpinolene, α-phellandrene and β-phellandrene.

7. The abrasive hand cleansing material of claim 5, wherein the blend of paramenthadienes is present in an amount of from 5 to 10% by weight.

8. The abrasive hand cleansing material of claim 1, wherein the oily emulsifiers are present in an amount of up to 15% by weight.

9. The abrasive hand cleansing material of claim 1, further comprising an antioxidant in the aqueous hand cleansing formulation in an amount of up to 0.5% by weight.

* * * * *